(12) United States Patent
Joshua et al.

(10) Patent No.: US 10,459,870 B2
(45) Date of Patent: Oct. 29, 2019

(54) MEDICAL DEVICE CONNECTIVITY INTERFACE SYSTEM AND METHOD

(71) Applicant: COVIDIEN LP, Mansfield, MA (US)

(72) Inventors: Dev Devanayagom Joshua, Superior, CO (US); Daniel Robbin Letcher, Brighton, CO (US); Aaron Damian Macan, Loveland, CO (US)

(73) Assignee: COVIDIEN LP, Mansfield, MA (US)

( * ) Notice: Subject to any disclaimer, the term of this patent is extended or adjusted under 35 U.S.C. 154(b) by 0 days.

(21) Appl. No.: 16/123,978

(22) Filed: Sep. 6, 2018

(65) Prior Publication Data
US 2019/0073333 A1 Mar. 7, 2019

Related U.S. Application Data (63) Continuation of application No. 15/197,300, filed on Jun. 29, 2016, now Pat. No. 10,095,649.
(Continued)

(51) Int. Cl.
*G06F 13/42* (2006.01)
*G06F 19/00* (2018.01)
(Continued)

(52) U.S. Cl.
CPC ...... *G06F 13/4234* (2013.01); *G06F 11/2289* (2013.01); *G06F 11/3051* (2013.01);
(Continued)

(58) Field of Classification Search
CPC ............ G06F 13/4234; G06F 11/2289; G06F 11/3051; G06F 19/00; G06F 19/3418;
(Continued)

(56) References Cited

U.S. PATENT DOCUMENTS

| 7,500,950 B2* | 3/2009 | Al-Ali ................ A61B 5/0002 600/300 |
| 2005/0086389 A1 | 4/2005 | Chang |

(Continued)

FOREIGN PATENT DOCUMENTS

| WO | 2010/035165 A2 | 4/2010 |
| WO | 2012/026922 A2 | 3/2012 |

OTHER PUBLICATIONS

Invitation and Partial International Search Report from PCT Application No. PCT/US2016/0404429 dated Sep. 14, 2016, 6 pgs.

*Primary Examiner* — Kerri L McNally
(74) *Attorney, Agent, or Firm* — Cantor Colburn LLP (57) ABSTRACT

A system includes a medical monitor having a sensor input responsive to a sensor signal representative of a physiological parameter; a processor that may calculate the physiological parameter from the sensor signal; an output port in communication with the processor to output medical data comprising the calculated physiological parameter in a first communication protocol; a removable interface having an input port receptive of the medical data in the first communication protocol; a memory storing code that may translate the medical data into a second communication protocol; and a first output port that may transmit the medical data in the second communication protocol to an external system that recognizes the second communication protocol and not the first communication protocol.

20 Claims, 6 Drawing Sheets

Related U.S. Application Data (60) Provisional application No. 62/187,674, filed on Jul. 1, 2015.

(51) Int. Cl.
  *G06F 11/22* (2006.01)
  *G06F 11/30* (2006.01)
  *H04L 29/08* (2006.01)
  *H04L 29/06* (2006.01)
  *G16H 40/67* (2018.01)
  *G16H 10/60* (2018.01)

(52) U.S. Cl.
  CPC .......... *G06F 19/00* (2013.01); *G06F 19/3418* (2013.01); *G16H 40/67* (2018.01); *H04L 67/12* (2013.01); *H04L 69/08* (2013.01); *G16H 10/60* (2018.01)

(58) Field of Classification Search
  CPC ........ G16H 40/67; G16H 10/60; H04L 67/12; H04L 69/08
  USPC ....................................................... 340/573.1
  See application file for complete search history.

(56) References Cited

U.S. PATENT DOCUMENTS

| | | |
|---|---|---|
| 2005/0108055 A1 | 5/2005 | Ott et al. |
| 2011/0090086 A1* | 4/2011 | Dicks .................... A61B 5/1112 340/573.4 |
| 2012/0136218 A1 | 5/2012 | Lee et al. |
| 2012/0157801 A1* | 6/2012 | Hoss .................. A61B 5/14503 600/309 |
| 2012/0191467 A1 | 7/2012 | LaPlante et al. |
| 2015/0234986 A1* | 8/2015 | Dantsker ............... H04W 48/18 705/2 |

\* cited by examiner

MEDICAL DEVICE CONNECTIVITY INTERFACE SYSTEM AND METHOD

CROSS REFERENCE TO RELATED APPLICATION

This application is a continuation of U.S. Non-Provisional application Ser. No. 15/197,300, entitled "Medical Device Connectivity Interface System and Method," filed Jun. 29, 2016, which claims the benefit of U.S. Provisional Patent Application No. 62/187,674, entitled "Medical Device Connectivity Interface System and Method," filed Jul. 1, 2015, the contents of each of which are herein incorporated in their entirety for all purposes.

BACKGROUND

The present disclosure relates generally to medical device systems and, more particularly, to connectivity interface systems for communication between medical devices and external data management systems.

This section is intended to introduce the reader to various aspects of art that may be related to various aspects of the present disclosure, which are described and/or claimed below. This discussion is believed to be helpful in providing the reader with background information to facilitate a better understanding of the various aspects of the present disclosure. Accordingly, it should be understood that these statements are to be read in this light, and not as admissions of prior art.

In the field of healthcare, caregivers (e.g., doctors and other healthcare professionals) often desire to monitor certain physiological characteristics of their patients. Accordingly, a wide variety of devices have been developed for monitoring many such characteristics of a patient. Such devices provide doctors and other healthcare personnel with the information they need to provide the best possible healthcare for their patients. As a result, such monitoring devices have become an indispensable part of modern medicine.

Monitoring devices are often configured as dedicated monitoring units (e.g., a stand-alone pulse oximetry monitor) with integral processing circuitry for receiving measurements from medical devices and converting these measurements into medical information that is meaningful to a clinician. In certain healthcare settings, multiple monitoring devices may be used to monitor a single patient. For example, depending on a condition of the patient, the patient may be monitored with a ventilator, a pulse oximeter, dialysis machine, or any other monitoring systems, and combinations thereof that facilitate diagnosis and treatment of the patient. The monitoring devices may transmit data (e.g., measurements) to external devices (e.g., a multi-parameter monitor, remote displays, electronic data management systems, etc.) that may be readily accessible to a care provider (e.g., the doctors and/or healthcare personnel) during treatment of the patient.

BRIEF DESCRIPTION

This disclosure provides connectivity interfaces that expand connectivity of medical devices to external systems having different functionalities, features, and communication protocols. The connectivity interface may include circuitry that translates data from one protocol to another protocol and transmits translated data to external systems. Additionally, the connectivity interface may include circuitry to change communication mechanisms between the medical devices, the connectivity interface, and the external systems. As such, the connectivity interface may bridge existing medical devices with various external systems. The connectivity interface may include algorithms for processing data and/or correlate information between disconnected systems, thereby providing meaningful information to a user of the medical devices. Additionally, the connectivity interface may provide an interface to perform serviceability on the medical device (e.g., download logs).

Thus, in accordance with a first aspect, a system includes a medical monitor having a sensor input responsive to a sensor signal representative of a physiological parameter; a processor that may calculate the physiological parameter from the sensor signal; an output port in communication with the processor to output medical data comprising the calculated physiological parameter in a first communication protocol; a removable interface having an input port receptive of the medical data in the first communication protocol; a memory storing code that may translate the medical data into a second communication protocol; and a first output port that may transmit the medical data in the second communication protocol to an external system that recognizes the second communication protocol and not the first communication protocol.

In accordance with another aspect, a method includes using a removable interface to receive a first input via a first communication mechanism. The first input is representative of a first medical device measurement generated from a first medical device system programmed in a first communication protocol. The method also includes using the removable interface to translate the first communication protocol to the second communication protocol to generate a translated medical device measurement; generate an output representative of the translated medical device measurement; and transmit the output via a second communication mechanism to an external system programmed in the second communication protocol.

Also disclosed herein is a distributed medical monitor includes a first removable interface having a first input port that may receive a signal from a medical monitor or a medical sensor; a processor that may calculate a physiological parameter based on the signal; and a first output port that may transmit data in a first communication protocol; a second removable interface having a second input port that may receive the data from the first removable interface in the first communication protocol; a memory storing code that may translate the data into a second communication protocol; and a second output port that may transmit the data in the second communication protocol to an external system separate from the medical monitor or medical sensor. The external system may recognize the second communication protocol and not the first communication protocol, and the second removable interface may not calculate the physiological parameter.

BRIEF DESCRIPTION OF THE DRAWINGS

Advantages of the disclosed techniques may become apparent upon reading the following detailed description and upon reference to the drawings in which.

DETAILED DESCRIPTION OF SPECIFIC EMBODIMENTS

One or more specific embodiments of the present techniques will be described below. In an effort to provide a concise description of these embodiments, not all features of an actual implementation are described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

Medical devices (e.g., sensors, monitoring systems, etc.) may be used to monitor a patient in a clinical environment. The medical devices collect information associated with physiological parameters such as, blood oxygen saturation, pulse rate, respiratory rate, blood pressure, tidal volume, among others that enable caregivers (e.g., a doctor, clinician, technician, etc.) involved in the patient's care to evaluate, diagnose, and treat the patient. It is not uncommon during treatment of the patient to use medical devices having different hardware and software platforms that may be proprietary to a manufacturer of the medical devices. However, the differences in hardware and/or software platforms may increase the complexity of patient monitoring because the medical devices may be unable to communicate with each other and/or data information systems (e.g., hospital information systems, electronic data management systems, etc.) used by caregivers to monitor and/or compile patient information in, for example, the patient's medical chart. The different hardware and/or software platforms may present challenges for communication between such systems and for administrators who seek to integrate various monitoring systems in a healthcare setting.

Additionally, rapid advancements in information system technology may present communication challenges between existing medical devices and external systems (e.g., electronic data management systems) that may be upgraded to include the more advanced information system technology. Moreover, it may be difficult for existing and/or future medical devices to keep up with the information system technology advancements due to quality testing and specification requirements set forth by regulating agencies that control medical devices used to diagnose and treat patients. For example, medical devices are built according to FDA or other regulatory specifications before being cleared for distribution into the market for patient use. Because such cleared systems may be expensive, hospitals or other treatment facilities may be reluctant to purchase new devices that may include additional functionality or features, including updated communications protocols. However, it may be difficult to upgrade existing devices, which may need to undergo regulatory clearance if modified from their cleared versions. Therefore, previous generation medical devices may not meet the connectivity requirements to communicate with external systems having more recent information system technology advances. For example, a previous generation medical monitor may not be capable of communicating patient data to enter a data stream for an electronic medical records system. Further, because each hospital may purchase electronic medical records system from different vendors, each individual electronic medical records system may use its own communications protocol. Accordingly, an individual monitor model may have to undergo separate regulatory clearance procedures for each communication upgrade specific to different types of electronic medical records system. With the rapid advancements in information system technologies, it may be prohibitively expensive for healthcare providers and device manufacturers to update existing medical devices to keep up with the information system technology advancements.

Accordingly, the present disclosure is generally directed towards connectivity interfaces that add functionality to existing medical devices and that may be relatively inexpensive so that the added functionality, when obsolete, may be easily upgraded with a newer version of a connectively interface. In this manner, the connectivity interfaces may be swapped out or replaced to change or add communication protocols, physical hardware interfaces between devices, device hardware (e.g., speakers, lights, displays) data processing capabilities, etc. Such embodiments may permit modification of a medical device model for use in different hospitals, healthcare facilities, and/or homes by providing communication protocols or other modifications specific for integration with the desired facility. In this manner, a base model of a medical device may have improved flexibility to be used in a variety of locations by coupling the medical device to the appropriate connectivity interface to add any missing or desired functionality.

Further, a connectivity interface may be used to create isolated or distributed medical devices in which certain functionality associated with limited or no regulatory clearance (e.g., hardware or communication components) is present on one or more connectivity interfaces while other functionality associated with a higher regulatory burden (physiological parameter calculation circuitry, alarm calculation circuitry) is maintained on one or more separate connectivity interfaces. These distributed connectivity interfaces may be coupled in parallel or in series to yield a medical monitoring system with desired data processing and physiological parameter calculation functionality as well as communication and connectivity software and hardware capabilities. In this manner, changes to features with lower regulatory burdens may take place by modifying or replacing dedicated connectivity interfaces without triggering regulatory review. In another embodiment, modifications to features may trigger regulatory review, such as data processing algorithms or alarm limit modifications, may be relatively less complicated relative changing such features in a standalone medical device. For example, a dedicated parameter calculation connectivity interface as provided herein may lack other hardware features that are generally present in standalone medical devices. As a result, because such a dedicated connectivity interface has fewer features to review, the connectivity interface may have shorter and/or less burdensome application requirements for clearance by regulatory agencies, e.g., the FDA.

Connectivity interfaces as provided herein may be implemented as a removable interface device that may be used to connect medical devices with external systems (e.g., third party medical devices, data management systems, personal devices, etc.) that have different hardware and/or software platforms that may otherwise be unable to communicate with each other. The removable interface device may translate and transmit patient information (e.g., physiological parameters) between the medical devices and external systems to facilitate patient monitoring and data logging for patient medical records. That is, the removable interface device may provide a communication bridge for the medical device to communicate with systems having different operating system protocols (e.g., hardware and/or software platforms). In one embodiment, the removable interface device may be a medical device data system (MDDS) that receives and stores patient information from various data sources, converts the patient information from one format to another, displays the patient information, and transmits the patient information to multiple systems that may be used during treatment of the patient. MDDS do not calculate physiological parameters and/or control functions or parameters of the medical devices to provide a diagnosis and/or treatment regime for the patient. As such, regulatory requirements established by the regulating agencies (e.g., FDA) do not apply to the removable interface device. Advantageously, the removable interface device may be updated to keep up with the advancements in information system technologies, and may be used to bridge existing medical devices with external systems having different hardware and/or software platforms. According, the removable interface device may improve and expand the connectivity of existing medical devices with external systems having advanced information technology. Such connectivity and communication between existing medical devices and updated external systems and/or third party medical devices is a benefit of the disclosed embodiments.

Figure 1:
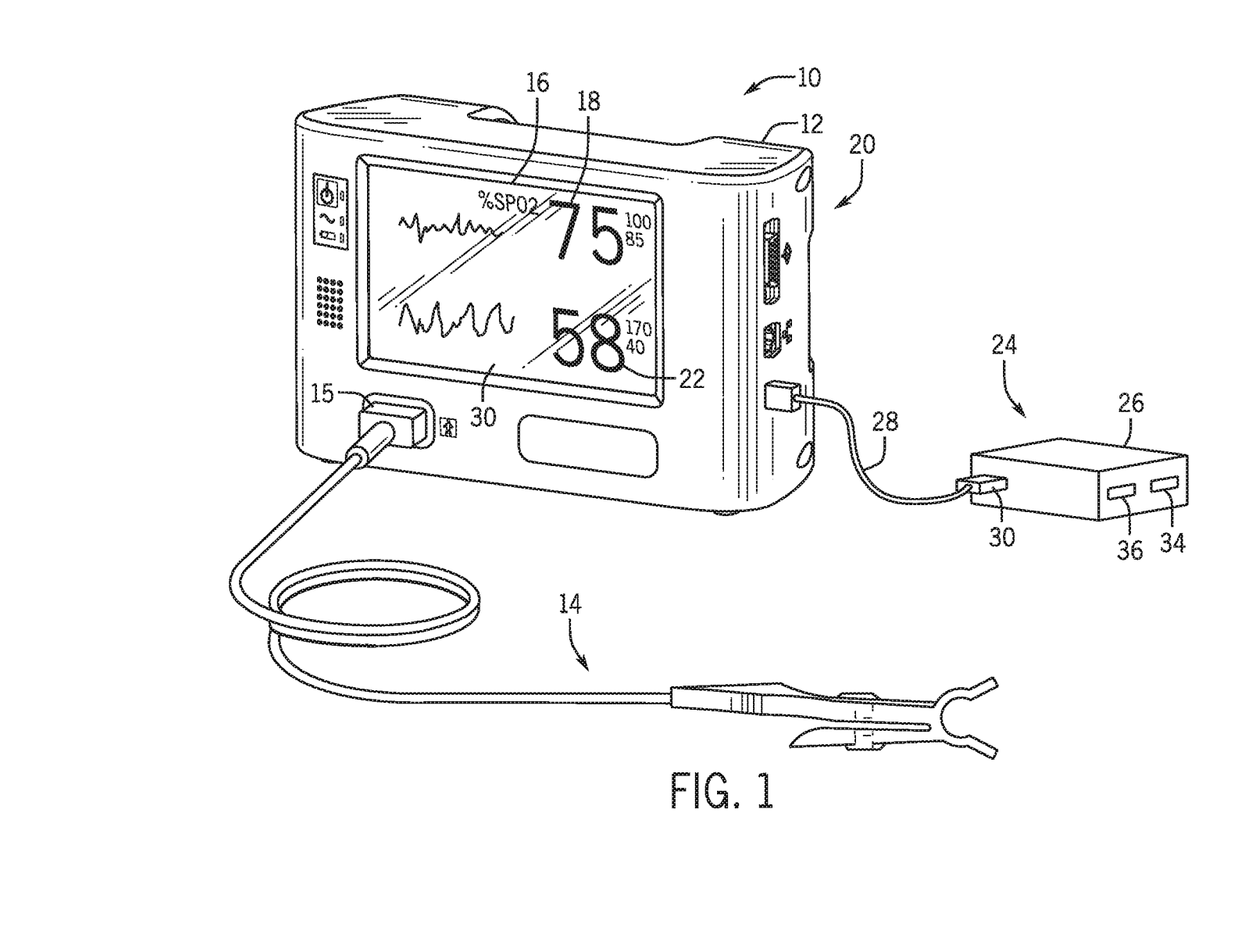
FIG. 1 is schematic diagram of a medical monitoring system having a medical device coupled to a removable interface device to facilitate connectivity and that receives and transmits physiological parameters generated by the medical device to external systems according to embodiments of the present techniques.

FIG. 1 illustrates a medical monitoring system 10 that may include connectivity interface devices to facilitate communication with external systems and/or devices having different hardware and/or software platforms, in accordance with an embodiment. In the illustrated example, the system 10 includes a standalone medical monitor 12. While the illustrated medical monitor 12 is shown in the context of pulse oximetry monitoring, the medical monitor 12 may also include regional oximeters, electroencephalography (EEG) monitors, capnography monitors, depth of anesthesia monitors, and monitors that measure blood pressure, temperature, glucose, tissue water fraction, and/or other parameters. Further, the monitor 12 may be a multi-parameter monitor or may be part of a distributed monitoring system under control of a central station. The monitor 12 is coupled to a sensor 14 for monitoring one or more physiological parameters of a patient. For example, the monitor 12 may receive a physiological signal from the sensor 14, and the monitor 12 may be configured to generate a physiological waveform and/or calculate or measure one or more physiological parameters based on the physiological signal.

In the illustrated example, the monitor 12 is a pulse oximetry monitor and the sensor 14 is a pulse oximetry sensor, such as those available from Covidien, L. P. or Medtronic. For example, the sensor 14 may include at least two emitters, which may emit light at two different wavelengths, and at least one detector for detecting photoplethysmography (PPG) signals from the patient tissue. The monitor 12 may include processing circuitry that, when invoked, is configured to execute code (e.g., stored in a memory of the monitor 12 or received from another device) for filtering and processing the signals from the sensor 14 to calculate physiological parameters, such as oxygen saturation ($SpO_2$) and pulse rate. In other embodiments, the monitor 12 may calculate or measure a different parameter or combination of parameters. For example, the monitor 12 may be a regional oximeter. In such an embodiment, the sensor 14 includes at least two emitters and at least two detectors for detecting PPG signals at different depths, and the monitor 12 receives the sensor signal at interface circuitry 15 and processes the PPG signals by invoking circuitry for physiological parameter calculation to calculate regional oxygen saturation ($rSO_2$). It should be appreciated that these are merely provided as examples, and other types of medical monitors may be used, such as the medical monitors noted above and multi-parameter monitors.

As illustrated in FIG. 1, the monitor 12 includes a display 16 displaying one or more calculated physiological parameters, such as oxygen saturation 18, heart or pulse rate 22, or tissue perfusion, EEG, temperature, respiration rate, end tidal carbon dioxide ($EtCO_2$), blood pressure, glucose, tissue water fraction, hemoglobin, or any other suitable physiological parameters. The display 16 may also display information related to alarms, such as oxygen saturation alarm thresholds or heart rate alarm thresholds, monitor settings, and/or signal quality. In certain embodiments, the display 16 may be a touch screen display. The monitor 12 also includes various ports 20 for connecting the medical monitoring system 10 to peripheral devices such as, but not limited to printers, flash drives, Ethernet cables, or any other suitable peripheral device.

In certain embodiments, at least one of the ports 20 is used to connect a connectivity interface, illustrated here as a removable interface device 24, to the system 10. The removable interface device 24 is configured to expand the connectivity of the system 10 to one or more external systems and/or devices. As shown, the removable interface device 24 is implemented to be removed and/or coupled to the monitor 12 by an operator. That is, the removable interface device 24 includes a separate housing 26 that may couple port 20 to input port 30 via cable 28. The housing 26 is separable and non-integral with the monitor 12, such that the removable interface device 24 may be removed or replaced as appropriate. The input port 30 and outputs 34, 36 may be disposed along a surface of the housing 26 of the removable interface device 24 that is accessible to an operator of the system 10 and/or other external systems such that the operator may readily link the removable interface device 24 with the desired systems. In certain embodiments, the removable interface device 24 may communicate with the monitor 12 and the other external systems wirelessly (e.g., via a unifying receiver, WiFi, or Bluetooth). In one embodiment, the communication is one-way. For example, the monitor 12 sends data to the removable interface device 24, which in turn sends data to external devices. The removable interface device 24 does not send data back to the monitor 12.

The removable interface device 24 may provide connectivity between the system 10 and the external systems, some of which may have different hardware and/or software platforms, by expanding the connectivity ports (e.g., by providing additional output ports 34, 36), translating data (e.g., the physiological parameters) from the system 10 into a protocol understood by the software platforms of the external systems, and changing communication mechanisms (e.g., serial, WiFi, Bluetooth, Ethernet, etc.) between the system 10, the removable interface device 24, and the external systems. For example, in certain embodiments, the system 10 may transmit patient information to the removable interface device 24 via a serial communication mechanism, and the removable interface device 24 may convert the serial communication mechanism to a WiFi communication mechanism before transmitting the patient information to the external system. That is, the removable interface device 24 may receive information via one communication mechanism and translate/transmit the information via a different communication mechanism. In this way, existing medical devices, such as the system 10, may be configured to communicate with external systems having a wide variety of communication interfaces and protocols.

Modifying components of medical devices, such as the system 10, to keep up with advances in information system technologies may require clearance according to FDA and other regulatory specifications. This may result in time to market delays for the modified/updated medical devices, and increased costs for healthcare providers. For example, the healthcare providers may need to replace the existing system 10 to enable communication with updated external systems (e.g., data management systems) and meet compatibility requirements for updated communication and connectivity protocols. The removable interface device 24 may provide a plug and play type mechanism between existing and future medical monitoring systems and software platforms. Therefore, the existing medical devices may not need to be replaced to keep up with the advances in information system technologies, thereby decreasing the overall cost associated with updating and replacing the existing medical devices. As discussed in detail below, the removable interface device 24 may house several network components within a housing 26 that facilitate communication between the system 10 and the external systems (e.g., multi-parameter monitors, electronic data management systems, personal devices, networks, etc.). While in the illustrated embodiment the removable interface device 24 is coupled to the system 10 via a cable 26, the removable interface device 24 may be coupled to the system 10 wirelessly, via a Universal Serial Bus (USB) male connector attached to the removable interface device 24, or any other suitable coupling system/device.

Figure 2:
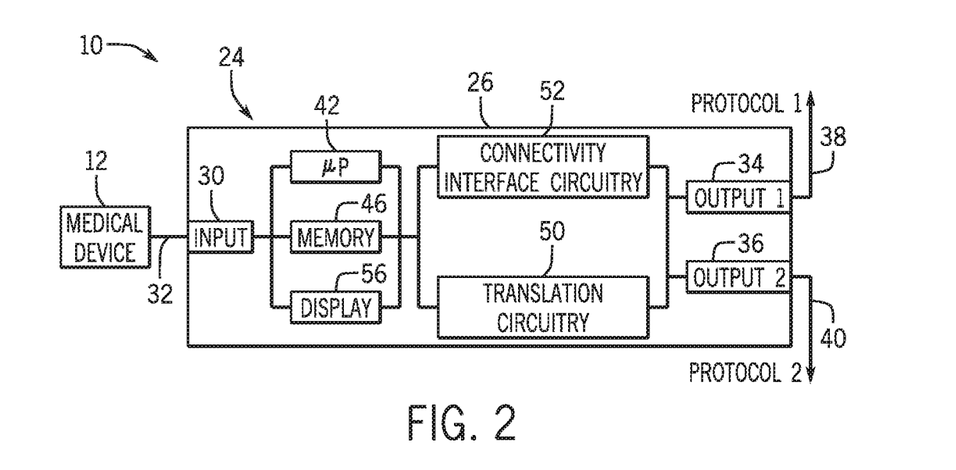
FIG. 2 is a block diagram of an embodiment of the removable interface device of FIG. 1.

FIG. 2 illustrates an embodiment of the removable interface device 24 that may be used to connect the system 10 with external systems/devices. In the illustrated embodiment, the removable interface device 24 includes one or more data communication links that enable the removable interface device 24 to connect to multiple systems such as, but not limited to, the system 10, a cellular or smart phone, tablet, other handheld device, laptop computer, monitor, server, cloud, or the like that may be configured to receive and store data and, in certain embodiments, show the data on a display associated with the system. For example, the removable interface device 24 includes an input 30 that joins the removable interface device 24 and the monitor 12, thereby allowing the removable interface device 24 to receive data from the monitor 12. The removable interface device 24 also includes outputs 34, 36 that transmit information (e.g., data 32) to external systems via different protocols. The input 30 and outputs 34, 36 may be configured for communication via a serial peripheral interface (SPI), a universal serial bus (USB) interface, a universal asynchronous receiver/transmitter (UART) interface, a Two Wire Interface (TWI) such as I2C, or an RS232 interface, a high definition multimedia interface (HDMI), Ethernet interface, or any other suitable communication link. In one embodiment, the output1 34 has a different communication mechanism configuration circuitry than the output2 36. For example, the output1 34 may be a USB port while the output2 36 is configured as an SPI. Further, in certain embodiments, the output1 34 and the output2 36 have different communication mechanism configuration circuitry than the input port 30.

As discussed above, the removable interface device 24 may transfer and/or exchange data (e.g., the data 32) with other systems/devices, for example, a third party medical device, a centralized patient data repository, electronic data management system, personal device (e.g., smart phone, laptop, etc.), network communication systems, etc. In addition, the removable interface device 24 may store and retrieve the data 32 from the system 10, and convert the data 32 from a protocol understood by the system 10 into one or more protocols understood by the other external systems, as shown by arrows 38, 40. In certain embodiments, the removable interface device 24 may be a medical device data system (MDDS) classified by the FDA as low-risk Class I devices. Devices classified as Class I by the FDA are not subject to regulatory controls and specifications, unlike the system 10, which may be classified as Class II or III. Class II or III clearance may be more complex, may require pre-market notification, and may require comparison with a predicate device and/or validation studies, which are costly and complex to arrange. Therefore, MDDS may be modified/updated to include advanced in information system technologies, once the advanced technologies become available, without market time delays associated with updating medical devices. Accordingly, costs associated with modifications to existing and/or future medical devices may be decreased.

The removable interface device 24 may include network components (e.g., hardware and software) that enable the removable interface device 24 to expand the connectivity of the system 10 to several external system and/or networks. For example, the removable interface device 24 may include a microprocessor 42 and a memory 46 within the housing 26. The memory 46 may be a tangible and non-transitory machine-readable medium or media having instructions recorded thereon for execution by the microprocessor 42. The set of instructions may include various commands that instruct the microprocessor 42 to perform specific operations such as the methods and processes of the various embodiments described herein. The set of instructions may be in the form of a software program or application that may facilitate communication between medical device systems having proprietary software platforms and external systems having a different software platform (e.g., third party medical devices, data management systems, personal devices, servers, cloud, etc.). The memory 46 may include volatile and non-volatile media implemented in any method or technology for storage of information such as computer-readable instructions, data structures, program modules, protocols, or other data. The memory 46 may include, but is not limited to, RAM, ROM, EPROM, EEPROM, or any other suitable storage medium.

The removable interface device 24 may communicate with multiple external systems, including the system 10, using, for example, the protocols 38, 40 understandable by the external systems. Accordingly, the removable interface device 24 includes translation circuitry 50 that translates the data 32 from the system 10 into the protocols 38, 40. The protocols 38, 40 may include, for example, proprietary protocols such as a Standard Host Interface Protocol (SHIP), the Phillips Interface Protocol (PIP), or any other suitable protocol depending on the software platform of the external systems. The removable interface device 24 may be preprogrammed to communicate using the protocols 38, 40 or may automatically select the particular protocol 38, 40 from among a variety of preprogrammed protocols. The translation to the protocols 38, 40 may be in parallel or in series.

In addition to the translation circuitry 50, the removable interface device 24 may include connectivity interface circuitry 52 that converts communication mechanisms (e.g., Serial, WiFi, Bluetooth, Ethernet) from one form to another form. For example, in certain embodiments, the communication mechanism between the system 10 and the removable interface device 24 is a Serial communication mechanism, and the communication mechanism between the removal interface device 24 and the external system is WiFi. The connectivity interface circuitry 52, converts the Serial communication mechanism to the WiFi communication mechanism. In this way, the removable interface device 24 may receive the data 32 via one communication mechanism (e.g., Serial, WiFi, Bluetooth, Ethernet) and transmit the data 32 via a different communication mechanism. The translation circuitry 50 and the connectivity interface circuitry 52 enable the removable interface device 24 to expand the connectivity of the system 10 to various external systems that may, otherwise, be unable to communicate with the system 10 due, for example, differences in hardware and/or software platforms. The removable interface device 24 may also include a display 56 that displays the patient's information (e.g., the data 32 and/or patient identification parameters from the system 10), connectivity information (e.g., which external devices are in range and/or connected to the removable interface device 24), wireless signal strength, battery life, etc.

Figure 3:
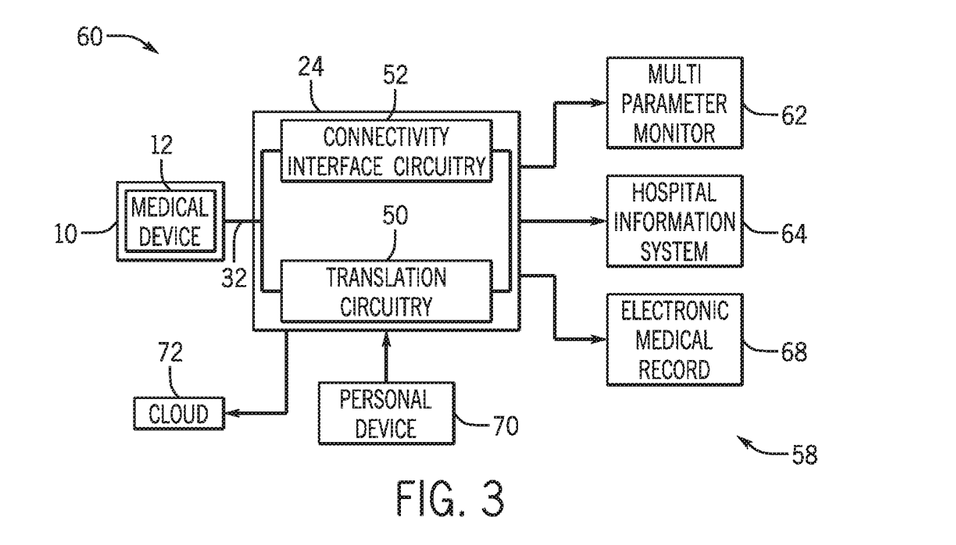
FIG. 3. is a block diagram of a removable interface device coupled to multiple external devices according to embodiments of the present techniques.

As discussed above, the removable interface device 24 may distribute (e.g., route) the data 32 from the system 10 to external systems that may have different operating hardware and/or software platforms. FIG. 3 is a block diagram of an embodiment of a network architecture 60 used in conjunction with the removable interface device 24. In the illustrated embodiment, the removable interface device 24 couples/links the system 10 with to various external systems 58. For example, the removable interface device 24 may link the system 10 to a multi-parameter monitor, hospital information system (HIS) 64 (e.g., Perfusion Record Systems, Anesthesia Record Systems, usage statistics systems, etc.), electronic medical record (EMR) 68, a personal device 70 (e.g., cell phone, smart phone, laptop, personal digital assistant (PDA), etc.), and/or cloud 72 that may be used by the physician and/or clinician to review the patient's information. The external system 58 may be within the patient's room or may be located remotely throughout the clinical setting. For example, the multi-parameter monitor 62 may be part of a centralized monitoring system that receives patient information from various medical devices used to monitor the patient. The centralized monitoring system may be located at a nurse's station that is away from the patient's room. Centralized monitoring systems may facilitate patient monitoring by allowing healthcare providers to continuously monitor the patient's physiological parameters without having to go into the patient's room or waiting for alarms to alert them of the patient's physiological parameters.

Similarly, routing the data 32 to the personal device 70 and/or cloud 72 may provide physicians and/or clinicians immediate access to the patient's information, thereby improving the efficacy of patient treatment and interaction. In certain embodiments, the remote interface device 24 may send alarms generated by the system 10 to the personal device 70 to alert the physician and/or clinician about a status of the patient. For example, the system 10 may trigger an alarm via the monitor 12 if the physiological parameter is above or below a desired threshold. The data 32 transmitted to the removable interface device 24 may contain information about the alarm and alert the physician and/or clinician by routing the data 32 to, for example, the personal device 70. Additionally, routing the data 32 from the system 10 to the HIS 64 and/or the EMR 68 may decrease delays and errors in medical record entries (e.g., chart entries) compared to, for example, manual data entry by healthcare personnel interacting with the patient. In certain embodiments, the removable interface device 24 may receive patient information from multiple patients. The removable interface device 24 may route the patient information for each patient to the respective external system 58 associated with each patient. That is, the removable interface device 24 may be a centralized unit (e.g., hub) for receiving and distributing the patient information.

HIS 64 and EMR 68 software platforms may be frequently updated and/or improved to keep up with advances in information technology and meet healthcare provider demands. Therefore, existing medical devices, such as the system 10, may be unable to communicate with the HIS 64 and/or EMR 68 after the update due to differences in software platforms resulting from the update. As discussed above, it may be difficult, and costly, for medical devices to be continuously modified/updated to keep up with information system technology improvements/advancements due, in part, to time to market delays resulting from regulatory requirements set forth by the FDA and other regulatory agencies. That is, the updated medical devices are required to pass clearance before they are available in the market for patient use. Clearing the medical devices for market may involve extensive quality testing and, by the time the medical device is cleared to market, new advancements in information technology may be available.

The removable interface device 24 may include a software platform that may allow connectivity between existing medical devices and databases associated with the HIS 64 and/or EMR 68. The software platform of the removable interface device 24 enables communication and transfer of information between the system 10 and the HIS 64 and/or EMR 68, even in situations where the HIS 64 and/or EMR 68 software platform is updated and/or changed. The software running on the removable interface device 24 may perform post processing applications such as, but not limited to, data synchronization, time stamping, etc. Accordingly, the removable interface device 24 may act as a communication interface between the existing medical devices and the HIS 64 and EMR 68. In this way, the existing and future medical devices, such as the system 10, may communicate with the external systems 58 despite the differences in hardware, software, and/or communication mechanisms resulting from advancements in information system technologies. In certain embodiments, the removable interface device 24 may be classified as a Class I medical device data system (MDDS). Therefore, the removable interface device 24 may not need to be cleared according to FDA regulations. That is, changes to the functionality of the system 10 implemented via the removable interface device 24 and that do not include any change to the sensor 14 or the physiological parameter algorithm may not trigger a requirement for a new clearance of the system 10 or the monitor 12. Accordingly, hardware and/or software platforms for the removable interface device 24 may be updated to keep up with the advancements in information system technologies, and may be available for use in the market in a short period of time compared to updating/modifying medical device platforms (e.g., hardware and/or software). In other embodiments, the removable interface device 24 may include physiological parameter calculation and/or alarm calculation functionality. In such embodiments, the removable interface device 24 may be cleared as a Class II or III device. In one embodiment, the removable interface device 24 may include functionality that upgrades and/or changes an algorithm of the system 10. In such embodiments, the upgrades and/or changes may trigger a new clearance. Such upgrades may include algorithms with improved motion performance, improved functionality at low perfusion, improved accuracy, improved signal confidence, etc. In addition, adding functionality of a new parameter calculation may also trigger a new clearance.

Figure 4:
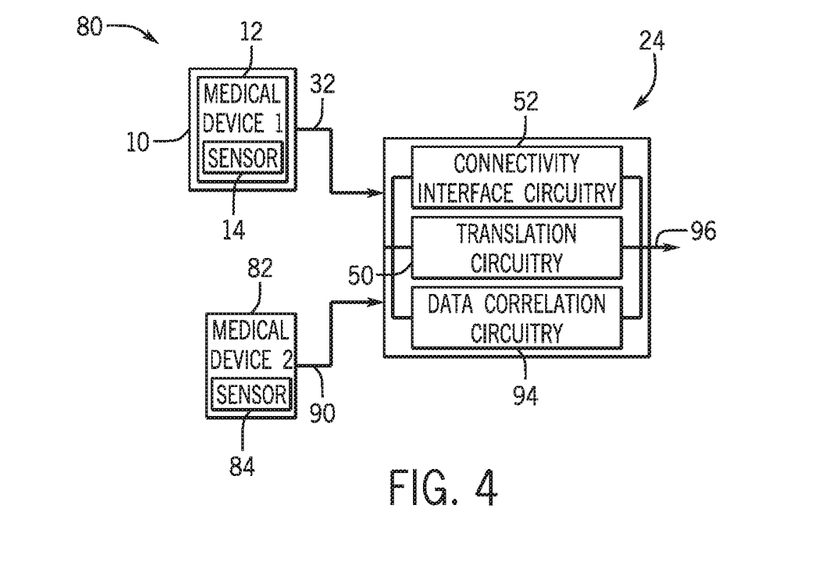
FIG. 4 is a block diagram of an embodiment of a removable interface device having data synchronization circuitry data for receiving data from medical sensors or devices according to embodiments of the present techniques.

In certain embodiments, the removable interface device 24 may couple multiple medical devices having different software platforms. FIG. 4 illustrates a multi-parameter medical monitoring system 80 that includes the system 10, having the monitor 12 and sensor 14 and using proprietary software platform, coupled to another medical monitor system 82 (e.g., a third party medical device), having a different software platform, via the removable interface device 24. The removable interface device 24 acts as a bridge between the systems 10, 82. Each system 10, 82 may monitor a single physiological parameter or multiple physiological parameters. By way of example, the system 10 may include the pulse oximetry sensor 14 and the medical device 82 may include a blood pressure sensor 84. As should be noted, the sensors 14, 84 may be any other suitable sensor such as, but not limited to, a temperature sensor, a pressure sensor, carbon dioxide sensor, and combinations thereof. As discussed above, the system 10 includes a proprietary software platform that may not be recognized by the system 82. As such, the system 10, 82 may be unable to communicate with each other. The removable interface device 24 may bridge the two system 10, 82 by translating the data 32 from the system 10 (e.g., via the translation circuitry 50) into a protocol that is recognized by the software platform in the medical device 82. Similarly, the removable interface device 24 may translate data 90 from the medical device 82 into a protocol that is understood by the proprietary software platform of the system 10.

Additionally, the removable interface device 24 may include data correlation circuitry 94 that may combine and correlate the data 32, 90 to provide meaningful data (e.g., data 96) that may be used to provide a complete assessment of the patient. Combining the data 32, 90 may allow healthcare personnel (e.g., physicians, clinicians, technicians, etc.) to determine a proper diagnosis and/or treatment for the patient. For example, in one embodiment, the medical monitoring system 80 may be used for autoregulation. Autoregulation is a physiological process that attempts to maintain an optimal cerebral blood flow to supply appropriate levels of oxygen and nutrients to the patient's brain. In autoregulation monitoring, a physician may monitor a patient's autoregulation through the use of various medical monitoring devices and systems, which may have different software platforms (e.g., the medical devices 12, 82). The patient's autoregulation may be monitored by correlating measurements of the patient's blood pressure (e.g., arterial blood pressure) with measurements of the patient's oxygen saturation (e.g., regional oxygen saturation). However, it may be difficult to correlate the patient's physiological measurements when the monitoring devices have different software platforms. The removable interface device 24 may facilitate communication between the various monitoring systems such that the measurements may be correlated. Further, the removable interface device 24 permits correlation of data from separate monitoring platforms without modification of each respective monitor. That is, the more complex monitors 12, 82, which are already approved via regulatory clearance, are upgraded for additional functionality via the removable interface device 24 while remaining physically unchanged. In the disclosed embodiment, the removable interface device 24 may undergo separate clearance as a Class II or III device. However, as the autoregulation or other correlated algorithm is upgraded or improved, the upgraded or replacement removable interface device 24 including the improved algorithm may be separately cleared while the monitors 12, 82, which are relatively more expensive, may be maintained without any change. In another embodiment, the data correlation circuitry 94 may correlate data from a single monitor (e.g., monitor 12) using an algorithm to calculate a parameter or indicator that the monitor does not have to improve the functionality of the monitor.

Figure 5:
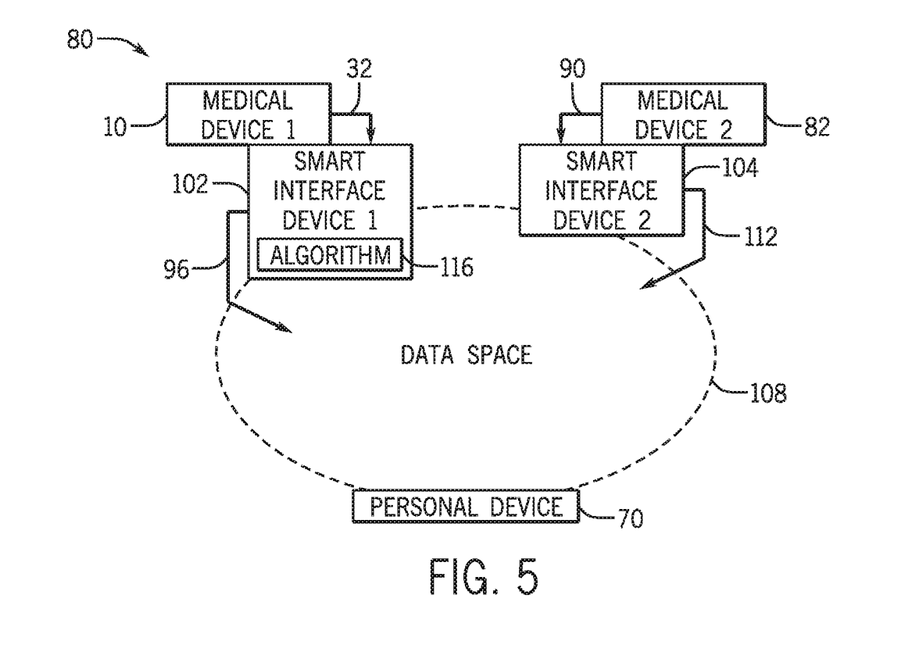
FIG. 5 is a block diagram of medical devices coupled to removable interface devices according to embodiments of the present techniques.

FIG. 5 is another embodiment of the medical monitoring system 80 that includes smart interface devices 102, 104 configured to correlate data from the medical devices 10, 82. In the illustrated embodiment, the smart interface devices 102, 104 enable communication between the medical devices 10, 82 through data space 108. Unlike the embodiment illustrated in FIG. 4, each system 10, 82 is coupled to a respective interface device 102, 104. That is, the medical devices 10, 82 have a dedicated interface device 102, 104 for receiving and/or transmitting patient information. The smart interface devices 102, 104 may be connected to the respective system 10, 82 via any suitable communication mechanism (e.g., Serial, WiFi, Bluetooth, Ethernet). The smart interface devices 102, 104 receive the data 32, 90 from the respective system 10, 82. The smart interface devices 102, 104 translate the data 32, 90, thereby generating translated data 96, 112, respectively. The smart interface devices 102, 104 transmit the translated data 96, 112 to the data space 108 for correlation (e.g., via dynamic discovery protocols). The personal device 70 may retrieve the correlated information from the data space 108 to assess the status of the patient. The personal device 70 may be a computer, laptop, smart phone, or any other suitable general purpose device configured to communicate with the data space 108 to receive the translated data 96, 112. The smart interface devices 102, 104 may time-stamp the translated signals 96, 112 before transmitting to the data space 108. This may enable the physician to determine changes in the data 32, 90 over time.

Figure 6:
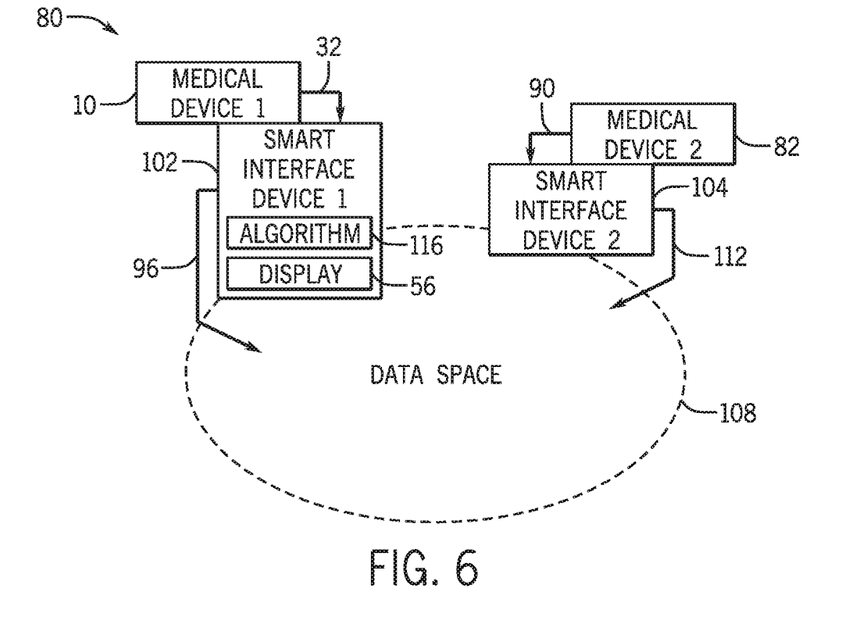
FIG. 6 is a block diagram of medical devices coupled to removable interface devices, whereby a removable interface device includes a display and data correlation algorithm circuitry according to embodiments of the present techniques.

In certain embodiments, at least one of the smart interface devices 102, 104 is configured for autoregulation monitoring. FIG. 6 illustrates an embodiment of the monitoring system 80 having at least one smart interference device 102, 104 configured for auto-regulation monitoring. In this particular embodiment, the smart interface device 102 retrieves the correlated information from the data space 108 and displays the correlated information on the display 56. By incorporating autoregulation monitoring into the smart interference device 102, 104, the complexity of the autoregulation monitoring system may be simplified. In addition, any healthcare provider involved in the treatment of the patient may view the autoregulation information while tending to the patient without having to access another device (e.g., the personal device 70) or when the personal device 70 is unavailable.

The smart interface devices 102, 104 may enable integration of algorithms stored in the systems 10, 82 with one or more algorithms 116 stored in the smart interface devices 102, 104. For example, in certain embodiments, the one or more algorithms 116 may include a respiration rate (RR) algorithm. The smart interface device 102, 104 may receive the data 32, 90 from the system 10, 82 and determine the respiration rate of the patient. The smart interface device 102, 104 may display the RR and the other physiological parameters associated with the data 32 (e.g., heart rate, oxygen saturation, etc.) on the display 56. In other embodiments, the smart interface device 102, 104 may transmit the physiological parameters determined by the system 10, 82 and the one or more algorithms 116 to the multi-parameter monitor 62, the HIS 64, the EMR 68, the personal device 70, cloud 72, the data space 108, a remote display, and combinations thereof. In certain embodiments, the medical devices 10, 82 may be coupled to multiple smart interface devices 102, 104, each having a different algorithm for a physiological parameter of interest.

The smart interface device 102, 104 may enable manufactures to release updated software platform features and algorithms to existing medical devices 10, 82 without having to replace the existing system 10, 82. For example, the smart interface device 102, 104 may be built to meet FDA and other regulating standards to obtain clearance. The cleared smart interface device 102, 104 may be supplied to healthcare providers or certified technicians with instructions on how to update the software platform and/or algorithms on the existing system 10, 82. In this way, medical device manufacturers and healthcare providers may decrease costs generally associated with the manufacture and purchase of updated medical devices. Additionally, the smart interface device 102, 104 may expand the functionality of single-parameter monitoring devices during, for example, clinical trial studies. For example, in certain clinical trial studies, various physiological parameters may need to be obtained to evaluate efficacy of future medical devices and/or pharmaceuticals. The smart interface device 102, 104 may provide features and algorithms that may not be standard to existing medical devices to expand the monitoring capabilities of the existing medical device. In this way, existing medical devices may be customized to monitor physiological parameters of interest during the clinical studies.

Figure 7:
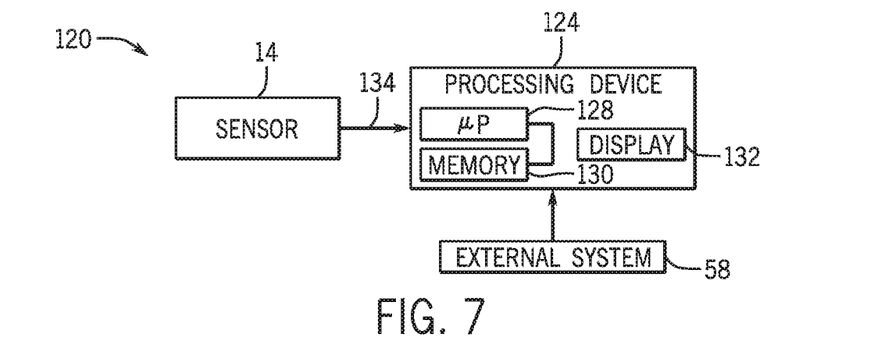
FIG. 7 is a block diagram of a removable interface device including data processing circuitry and coupled to a sensor according to embodiments of the present techniques.
Figure 8:
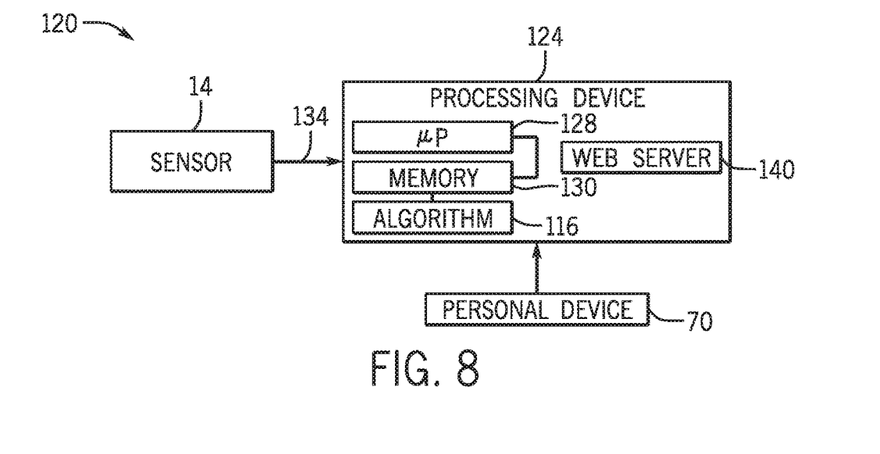
FIG. 8 is a block diagram of a removable interface device including data processing circuitry and a web server and further coupled to a sensor according to embodiments of the present techniques.

In certain embodiments, the smart interface device 102, 104 may be used in place of the monitor 12. In this particular embodiment, the smart interface device 102, 104 includes the components of the monitor 12, such as the processor, memory, proprietary software platform, and any other system component that may be used to determine the physiological parameters of the patient. FIG. 7 illustrates a medical monitoring system 120 including the sensor 14 and mini-processing device 124. The mini-processing device 124 may be dimensioned such that the mini-processing device 124 is wearable by the patient and/or healthcare personnel, attached to the patient's bed, or disposed (e.g., piggy backed) on the sensor (e.g., the sensor 14). The mini-processing device 124 includes a microprocessor 128, a memory 130, and a display 132. The memory 130 includes algorithms, code, and software instructions executable by the microprocessor 128 for filtering and processing a raw signal 134 to calculate and determine one or more physiological parameters of the patient. The removable interface device 124 may display physiological parameters 136 on the display 132. However, in certain embodiments, the mini-processing device 124 may not include the display 132. For example, as illustrated in FIG. 8, the removable interface device 124 may transmit the physiological parameters 136 to a server 140 (e.g., a web server). The physician may connect to the server 140 with the personal device 70 to retrieve the physiological parameters 136 from the server 140.

The mini-processing device 124 may communicate with the HIS 62, EMR 64, the personal device 70, cloud 72, or any other suitable external device, and combinations thereof to transmit the calculated physiological parameters and/or usage statistics for the medical device (e.g., number of use hours). For example, in certain embodiments, the memory 46 of the mini processing device 124 may store software which, when the mini processing device 124 is connected to the monitor 12, the software provides instructions to provide the external system 58 with usage statistics (such as number of hours of use) for the medical device 10 to either healthcare providers and/or a manufacturer of the medical device. Accordingly, the manufacturer may monitor the usage of the medical device 10, and charge the healthcare provider on usage instead of purchasing, for example, a new monitor. Additionally, healthcare providers may also monitor usage of the medical device 10 to determine inventory requirements for the medical device 10 in clinical settings.

While in the illustrated embodiment the mini-processing device 124 is coupled to a single sensor 14, the mini-processing device 124 may be coupled to multiple sensors 14. The coupling between the sensor 14 and the mini-processing device 124 may be a wired or wireless connection. In certain embodiments, the mini-processing device 124 may be worn by the patient. For example, the mini-processing device 124 may be a button or clip that is pinned onto the patient's garment, a wrist band, necklace, or any other suitable wearable object. Attaching the mini-processing device 124 to the patient may facilitate patient monitoring when the patient is transferred from one clinical setting to another. The mini-processing device 124 may continuously to track the patient's physiological parameters independent of the transfer. For example, in certain situations, the patient may be decoupled from the monitoring system during transfer from one clinical setting (e.g., the patient's room) to another clinical setting (e.g., imaging, surgery, etc.) and reconnected to another localized monitoring system.

However, with the mini-processing device 124, the patient may remain connected to the monitoring system 120 at all times during treatment. In this way, the monitoring system 120 may continue to monitor the patient without any interruptions resulting from moving the patient from one location to another. The mini-processing device 124 may include safety features that block the patient and individuals not involved in the patient's care from accidentally changing the settings and/or disabling the mini-processing device 124.

Figure 9:
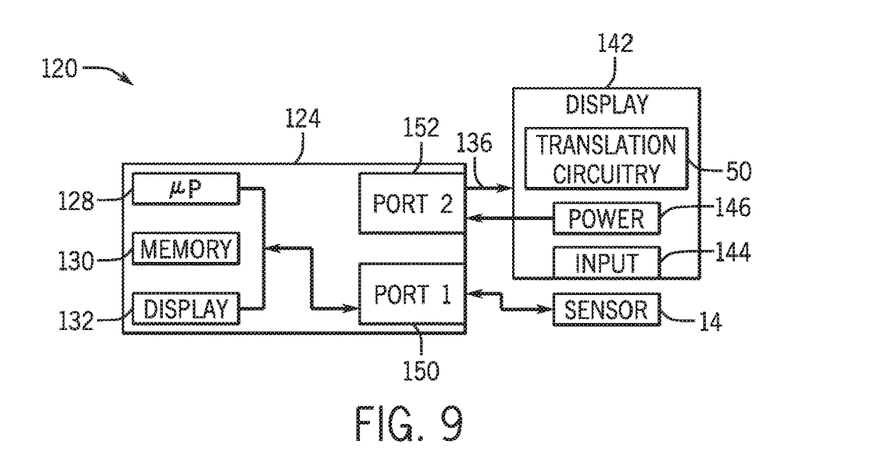
FIG. 9 is a block diagram of a removable interface device coupled to a remote display according to embodiments of the present techniques.

The mini-processing device 124 may also transmit the physiological parameters 136 to an external display. FIG. 9 illustrated an embodiment of the medical monitoring system 120 including an external display 142 (e.g., a TV). The removable mini-processing device 124 may communicate with the external display 142 via a wired (e.g., with a cable) or wireless (e.g., WiFi, Bluetooth) connection. The external display 142 may include an input device 144 (e.g., a touch screen) that may be used to change settings and/or silence alarms on the mini-processing device 124. In certain embodiments, the external display 142 may be in a remote location (e.g., at a nurses station), and may be used as a remote control for the mini-processing device 124. As such, the clinicians treating the patient may adjust the settings and/or silence the alarms of the mini-processing device 124 remotely.

The external display 142 may also include the translation circuitry 50 and connectivity interface circuitry 52 to facilitate communication between the mini-processing device 124 and other medical devices (e.g., anesthesia monitoring systems, perfusion monitoring systems, etc.) that are monitoring the patient, which may be operating with a different software platform. The external display 142 may receive and transmit the patient information (e.g., physiological parameters) from the other medical devices to the mini-processing device 124 to be logged with the physiological parameters 136. Similarly, the external display 142 may send the physiological parameters 136 from the mini-processing device 124 to the other medical devices and/or the multi-parameter monitor 62, the HIS 34, the EMR 68, the personal device 70, cloud 72, and/or server 140, thereby expanding the connectivity of the mini-processing device 124 to the external systems 58.

The mini-processing device 124 may include multiple ports 150, 152 to enable communication between the sensor 14 and the external display 142. The ports 150, 152 may have serial interfaces (e.g., USB, HDMI, Ethernet) to facilitate coupling to the sensor 14 and external display 142. In certain embodiments, the ports 150, 152 may be used to provide a wired connection (e.g., using, for example, a coax cable) between the mini-processing device 124 and the sensor 14 and/or external display 142. In other embodiments, a unifying receiver may be disposed in the ports 150, 152 to enable wireless communication between the mini-processing device 124, the sensor 14, and/or the external display 142.

To facilitate wireless communication between the external display 142 and the mini-processing device 124, the external display 142 may include pairing features. For example, once the mini-processing device 124 and the external display 142 are turned on, an operator (e.g., the clinician) may open a pairing menu on the external display 142. The pairing menu indicates devices that are within a range that the external display 142 can operate with. For example, the external display 142 may use dynamic discovery protocols to locate all the devices (e.g., patient monitoring systems, electronic data management systems, servers, personal devices, routers, etc.) within range of the external display 142. The operator may select to connect to, for example, the mini-processing device 124 from the pairing menu. Once the mini-processing device 124 is selected, the mini-processing device 124 may display a prompt to accept the pairing. Once accepted, mini-processing device 124 and the external display 142 are linked, and the external display 142 may begin to receive and transmit patient information to the mini-processing device 124. As should be noted, the mini-processing device 124 may also include similar pairing features to enable communication with multiple sensors used during patient monitoring.

The mini-processing device 124 may have low power requirements compared to, for example, the monitor 12. Therefore, the mini-processing device 124 may be powered by a general-purpose battery (e.g., alkaline, silver oxide, lithium, nickel, etc.). The general-purpose battery may be disposable or rechargeable. In certain embodiments, the mini-processing device 124 may be configured to receive AC power from an outlet. For example, the mini-processing device 124 may be configured to be plugged into the wall or a power cable that plugs to the AC power outlet. In other embodiments, the mini-processing device 124 may receive power 146 from the external display 142 (e.g., via a wired connection), as illustrated in FIG. 9.

Figure 10:
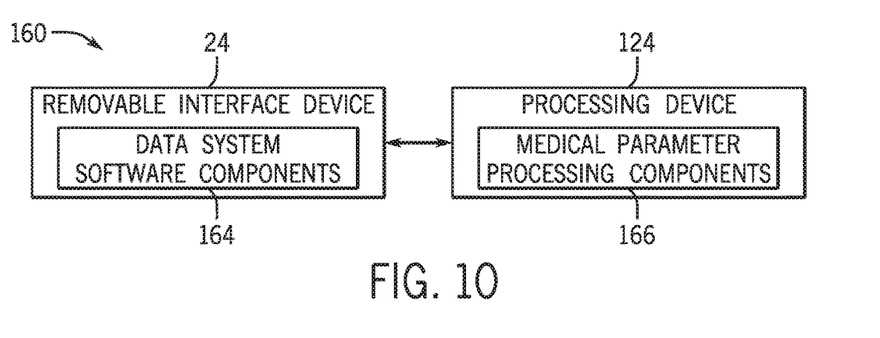
FIG. 10 is a block diagram of removable interface devices coupled in series and with different functionality according to embodiments of the present techniques.

In certain embodiments, the mini-processing device 124 may include the removable interface device 24 to generate a distributed monitoring system. For example, FIG. 10 illustrates a distributed monitoring system 160 that includes the mini-processing device 124 having medical parameter processing components 162, and the removable interface device 24 that includes data system software components 164. The medical parameter processing components 162 include proprietary software (e.g., code, instructions, algorithms, etc.) used to determine a patient's physiological parameters to facilitate patient diagnosis and treatment. The data system software components 164 of the removable interface device 24 includes instructions for transmitting, translating (e.g., via the translation circuitry 50), and modifying communication mechanisms (e.g., via the connectivity interface circuitry 52) of patient information between the mini-processing device 124 and other external devices (e.g., the multi-parameter monitor 62, the HIS 64, the EMR 68, the personal device 72, cloud 72, the server 140, etc.).

Figure 11:
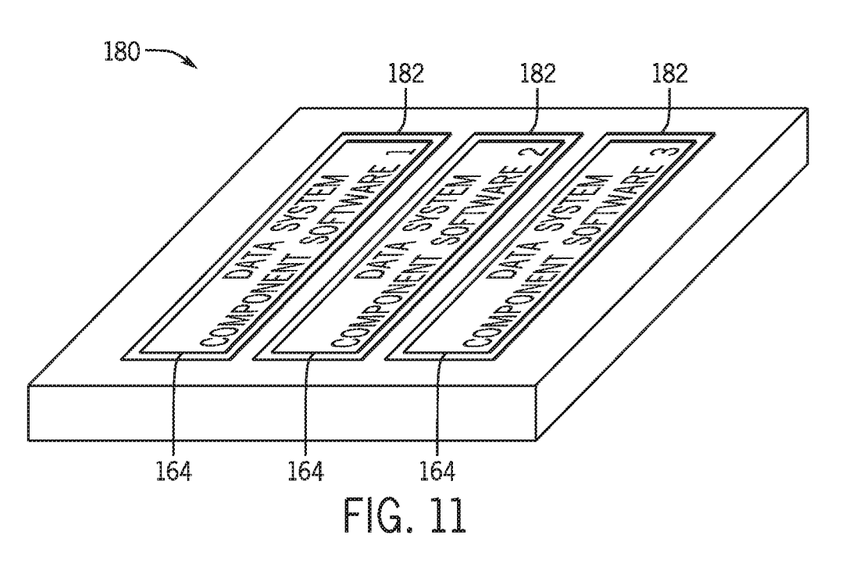
FIG. 11 is a schematic diagram of a removable interface device kit having separate removable interfaces devices with respective different software platforms for communicating with various external devices according to embodiments of the present techniques.

As discussed above, devices that determine physiological parameters used to diagnose and treat patients have to be cleared according to regulations set forth by the FDA and other regulatory agencies. Therefore, any changes to the mini-processing device 124 to keep up with advancements in information system technologies would require clearance. However, by coupling the removable interface device 24 to the mini-processing device 124, the data system software components 164 of the removable coupling device 24 may be updated without having to go through clearance, thereby expanding the connectivity of the mini-processing device 124 to external device that it would otherwise not be able to communicate with due, in part, to differences in hardware and/or software platforms. The removable interface device 24 may be provided as part of a kit 180 of multiple removable interface devices 182 having different data system software components 164 (e.g., updated software), as illustrated in FIG. 11. Healthcare providers may select the removable interface device 24 that has the desirable data system software component 164 meets the connectivity requirements to enable existing medical devices (e.g., the system 10, 82 and/or the mini-processing device 124) to communicate with the external devices 58, such as those discussed above with reference to FIGS. 3, 7, and 8. In certain embodiments, the data system software components 164 may be customized based on the needs and demands of the healthcare providers.

Upon receipt of the kit 180, the healthcare provider selects the removable device 24 that best matches the connectivity instructions/protocols to communicate with upgraded devices and/or systems. The provider removes the removable interface device 24 from the existing device 10, 82, 124. For example, the provider may detach the removable interface device 24 from a wired connection (e.g., cable), unifying receiver, etc. to block communication between the removable interface device and the existing device 10, 82, 124. Once the removable interface device 24 is decoupled from the existing device 10, 82, 124, the provider couples the selected removable interface device 182 to the existing device 10, 82, 124. Using, for example, dynamic discovery or other linking mechanism, the selected removable interface device 182 may indicate (e.g., on the display 56) the external systems 58 that are in range. The provider may select which external devices and/or systems to link with the selected interface device 182. In other embodiments, the provider may link the external systems 58 and the selected removable interface device 182 through controls and/or settings on the external systems 58.

Figure 12:
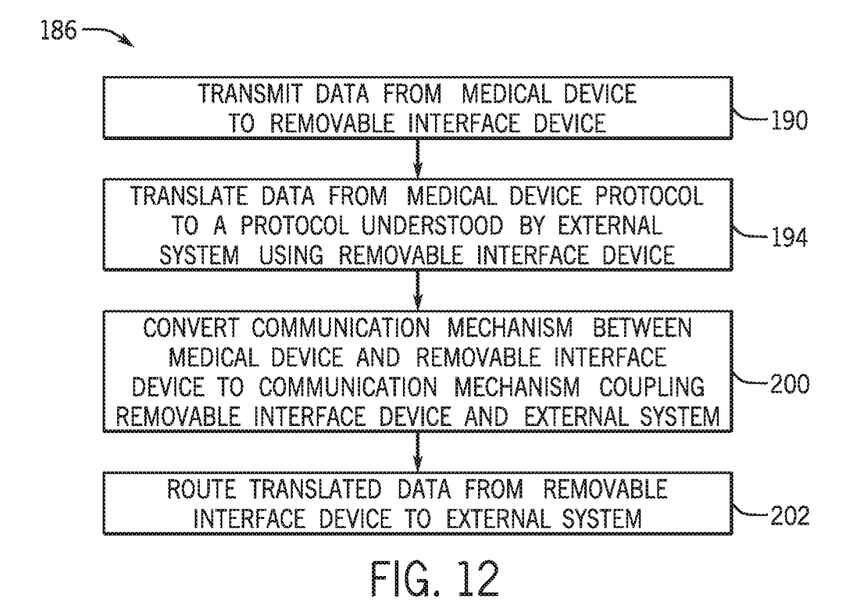
FIG. 12 is a flow diagram of a method for transmitting physiological parameters via a removable interface device according to embodiments of the present techniques.

As discussed above, the removable interface device 24 may expand connectivity for existing devices 10, 82, 124 to keep up with continuously changing information systems resulting from advances in information technology. Accordingly, present embodiments also include a method that utilizes the removable interface device 24 to enable communication and data flow between system having different hardware and/or software platforms. FIG. 12 illustrates a flow diagram of a method 186 by which the removable interface device 24 connection and communication flexibility between the existing devices 10, 82, 124 and the external devices discussed above with reference to FIGS. 3, 7, and 8. The method 186 includes transmitting the data 32, 90 from the existing system 10, 82, 124 to the removable interface device 24 (block 190), as discussed above with reference to FIG. 2.

The method 186 also includes translating the data 32, 90 from a first protocol to a second protocol understood by the external systems 58 (block 194). The existing medical devices 10, 82, 124 operate using proprietary software that may not be recognized by the external systems 58. As such, transferring patient information between the existing system 10, 82, 124 and any one of the external systems 58 may be difficult. In addition, due, in part, to advancements in information system technologies, healthcare providers may update the external systems 58 periodically. The updated external systems 58 may have hardware and/or software platforms that may be unable to connect to the existing system 10, 82, 124. However, because medical devices are built according to FDA and other regulatory specifications, modifications to the existing system 10, 82, 124 and/or development of future medical devices to include advanced information system technologies require clearance, which may result in time to market delays. Therefore, by the time the modified and/or future medical devices are available for use in a clinical setting, new advancements in information technology systems may be available and used by the external systems 58. The removable interface device 24 is configured to translate (e.g., via the translation circuitry 50) the patient information from the system 10, 82, 124 into a form that is understood by the updated external systems 58.

The method 186 also includes converting the communication mechanism (e.g., serial (USB, HDMI, etc.), WiFi, Bluetooth, Ethernet, etc.) between the existing system 10, 82, 124 and removable interface device 24 to a communication mechanism used to couple the removable interface device 24 and the external systems 58 (block 200). The removable interface device 24 include connectivity interface circuitry (e.g., the circuitry 52) that may convert the communication mechanism between the existing system 10, 82, 124 into another communication mechanism that enables communication between the removable interface device 24 and the external systems 58. For example, the interface circuitry 52 may convert a serial communication mechanism into a wireless (e.g., WiFi, Bluetooth) communication mechanism or vice versa. The method 186 also includes routing the translated patient information from the removable interface device 24 to one or more external systems 58 using the converted communication mechanism (block 202).

As described above, a removable interface device, such as the removable interface device 24, provides a path to allow communication between medical devices and external systems that have different hardware and/or software platforms. The removable interface device may expand the connectivity of existing medical devices that have different hardware and/or software platforms from external systems that may be used to monitor and/or log patient information (e.g., physiological parameters) during patient treatment. For example, because medical devices are cleared according to regulatory specifications, existing and future medical devices may not include the most recent information system technologies. As such, medical devices may be unable to communicate with external systems having more advanced information system technologies. The removable interface device as provided herein may mitigate the disconnectedness between the systems having different hardware and/or platform software. In certain embodiments, the removable interface device is considered a Class I device, and therefore does not need to meet regulatory specifications. As such, the removable interface device may keep up with the advancements in information technology systems, and enable communication between existing medical devices and updated external systems. In other embodiments, the removable interface device may be a Class II or III device.

What is claimed is:

1. A method, comprising:
    using a first removable interface device to:
        receive first medical data, via a first input port, from a first medical monitor communicatively coupled to a first medical sensor;
        translate the first medical data from a first communication protocol to a second communication protocol to generate first translated medical data;
        transmit the first translated medical data to an external system; and
    using a second removable interface device communicatively coupled to the first removable interface to:
        receive second medical data, via a second input port, from a second medical monitor communicatively coupled to a second sensor;
        translate the second medical data from a third communication protocol to the second communication protocol to generate second translated medical data; and
        transmit the second translated medical data to the external system.

2. The method of claim 1, comprising using the first removable interface device and the second removable interface device to time-stamp the first translated medical data and the second translated medical data, respectively.

3. The method of claim 1, comprising correlating the first translated medical data and the second translated medical data to generate correlated patient data.

4. The method of claim 3, comprising using the second removable interface device to retrieve the correlated patient data.

5. The method of claim 4, comprising displaying the correlated patient data on a display of the second removable interface device.

6. The method of claim 1, comprising using the first removable interface device to update a software platform of the first medical monitor with an updated software platform stored in a memory of the first removable interface device.

7. The method of claim 1, comprising using the second removable interface device to update a software platform of the second medical monitor with an updated software platform stored in a memory of the second removable interface device.

8. The method of claim 1, wherein the first removable interface device or the second removable interface device is a Federal Drug Administration (FDA) Class II or Class III device.

9. The method of claim 1, wherein at least one of the first removable interface device or the second removable interface device are a Federal Drug Administration (FDA) Class I device.

10. A system, comprising:
a first medical monitor coupled to a first medical sensor and a first removable interface device, the first removable interface device comprising:
a first input port configured to receive first medical data from the first medical sensor via the first medical monitor;
first translation circuitry configured to translate the first medical data from a first communication protocol to a second communication protocol to generate first translated medical data; and
first communication circuitry configured to transmit the first translated medical data to an external system; and
a second medical monitor coupled to a second medical sensor and a second removable interface device, the second removable interface device comprising:
a second input port configured to receive second medical data from the second sensor via the second medical monitor;
second translation circuitry configured to translate the second medical data from a third communication protocol to the second communication protocol to generate second translated medical data; and
second communication circuitry configured to transmit the second translated medical data to the external system.

11. The system of claim 10, wherein the first communication circuitry, the second communication circuitry, or both, are configured for wireless communication.

12. The system of claim 10, wherein the external system comprises a personal device.

13. The system of claim 10, wherein the first translated medical data and the second translated medical data are translated to the external system via a data space.

14. A system, comprising:
a first medical monitor communicatively coupled to a first medical sensor, wherein the first medical monitor is configured to receive a first signal from the first medical sensor, determine a first physiological parameter based on the first signal via a first software platform, and output first medical data comprising the first physiological parameter via a first communication protocol;
a second medical monitor communicatively coupled to a second medical sensor, wherein the second medical monitor is configured to receive a second signal from the second medical sensor, determine a second physiological parameter based on the second signal via a second software platform different from the first software platform, and output second medical data comprising the second physiological parameter via a second communication protocol;
a removable interface device communicatively coupled to the first medical monitor and the second medical monitor, wherein the removable interface device is configured to bridge the first medical monitor and the second medical monitor such that the first medical monitor is communicatively coupled to the second medical monitor, and wherein the removable interface device comprises:
an input port configured to receive the first medical data from the first medical monitor; and
a memory storing code configured to translate the first medical data from the first communication protocol to the second communication protocol or a third communication protocol to generate first translated medical data.

15. The system of claim 14, wherein the removable interface device comprises communication circuitry configured to transmit the first translated medical data and the second medical data to an external system.

16. The system of claim 15, wherein the external system comprises a multi-parameter monitor, a HIS, electronic medical records, a personal device, cloud, data space, a remote display, or any combination thereof.

17. The system of claim 15, wherein the communication circuitry is configured for wireless communication.

18. The system of claim 15, wherein the code of the removable interface device is configured to translate the second medical data to the third communication protocol before transmitting to the external system.

19. The system of claim 14, wherein the removable interface device comprises data correlation circuitry configured to correlate the first translated medical data and the second medical data.

20. The system of claim 14, wherein the first medical sensor is different from the second medical sensor, and wherein the first medical sensor comprises at least one of a pulse oximetry sensor, a blood pressure sensor, a temperature sensor, a pressure sensor, or a carbon dioxide sensor.

* * * * *